United States Patent [19]
Moriya et al.

[11] Patent Number: 5,932,457
[45] Date of Patent: Aug. 3, 1999

[54] PROCESS FOR PRODUCING D-PANTOIC ACID AND D-PANTOTHENIC ACID OR SALTS THEREOF

[75] Inventors: Takeo Moriya, Minoo; Yuichi Hikichi, Tsukuba; Yumiko Moriya, Minoo; Takamasa Yamaguchi, Kobe, all of Japan

[73] Assignee: Takeda Chemical Industries, Ltd, Osaka, Japan

[21] Appl. No.: 08/750,983

[22] PCT Filed: Sep. 11, 1996

[86] PCT No.: PCT/JP96/02585

§ 371 Date: Jan. 8, 1997

§ 102(e) Date: Jan. 8, 1997

[87] PCT Pub. No.: WO97/10340

PCT Pub. Date: Mar. 20, 1997

[30] Foreign Application Priority Data

Sep. 13, 1995 [JP] Japan .................................. 7-235065

[51] Int. Cl.⁶ ................................ C12P 7/42; C12P 7/40; C12N 1/20; C12N 15/00
[52] U.S. Cl. .................... 435/146; 435/136; 435/252.33; 435/320.1
[58] Field of Search ..................................... 435/136, 146, 435/320.1, 252.3, 252.33; 935/22; 536/23.2

[56] References Cited

FOREIGN PATENT DOCUMENTS 0 356 739   8/1989   European Pat. Off. .
0 493 060 A2  12/1991  European Pat. Off. .
0 590 857 A2  9/1993   European Pat. Off. .

OTHER PUBLICATIONS

Keilhauer et al., Isoleucine Synthesis in *Corynebacterium glutamicum*: Molecular Anlaysis of the ilvB–ilvN–ilvC Operon, *Journal of Bacteriology*, Sep. 1993, vol. 175, No. 17, pp. 5595–5603.

Primerano et al., "Role of Acetohydroxy Acid Isomeroreductase in Biosynthesis of Pantothenic Acid in *Salmonella typhimurium*", *Journal of Bacteriology*, Jan. 1983, vol. 153, No. 1, pp. 259–269.

Lawther et al., "The complete nucleotide sequence of the ilvGMEDA operon of *Escherichia coli* K–12", *Nucleic Acids Research*, 1987, vol. 15, No. 5, pp. 2137–2155.

Ingraham et al., "*Escherichia Coli* and *Salmonella Typhimurium*", *Cellular and Molecular Biology*, vol. 1, 1987, pp. 352–367.

*Primary Examiner*—Robert A. Wax
*Assistant Examiner*—Einar Stole
*Attorney, Agent, or Firm*—Foley & Lardner

[57] ABSTRACT

There is disclosed a process for producing D-pantoic acid or D-pantothenic acid utilizing the capability of the microorganism to synthesize D-pantoic acid or D-pantothenic acid. According to this process, (a) D-pantoic acid is biosynthesized from various carbon sources such as glucose to accumulate it in the culture medium, or (b) β-alanine is contacted with the microorganism by, for example, adding β-alanine to the culture medium, to cause condensation of the biosynthesized D-pantoic acid with β-alanine to accumulate D-pantothenic acid in the medium.

3 Claims, 1 Drawing Sheet

PROCESS FOR PRODUCING D-PANTOIC ACID AND D-PANTOTHENIC ACID OR SALTS THEREOF

FIELD OF THE INVENTION

The present invention relates to a novel process for producing D-pantoic acid and/or D-pantothenic acid, or a salt thereof. Pantothenic acid is useful as vitamin, and D-pantoic acid is useful as an important intermediate for the production of pantothenic acid or CoA.

BACKGROUND OF THE INVENTION

D-pantothenic acid is useful as vitamin. Prior art processes for producing D-pantothenic acid include (1) a process which comprises optically resolving DL-pantolactone and chemically condensing the resulting D-pantolactone with β-alanine or a salt thereof in methanol, (2) a process which comprises hydrolyzing a D-pantothenic acid ester with a microorganism or enzyme to obtain D-pantothenic acid, or selectively hydrolyzing only D-isomer of a DL-pantothenic acid ester to obtain D-pantothenic acid (JP-A 1-228487, JP-A 1-228488), (3) a process which comprises contacting potassium D-pantoate, β-alanine and ATP with resting cells of a microorganism or an enzyme thereof in tris buffer (Journal of Biological Chemistry, Vol. 198, p.23 (1952), Abstracts of Papers 176th American Chemical Society National Meeting, Division of Microbial and Biochemical Technology, Vol. 48 (1978), etc.), (4) a process which comprises culturing a particular microorganism in the presence of DL-pantoic acid and β-alanine and specifically condensing D-pantoic acid with β-alanine to obtain D-pantothenic acid (JP-A 5-23191), and (5) a process which comprises culturing a particular microorganism in the presence of β-alanine to obtain D-pantothenic acid (JP-A 6-261772).

Processes for producing D-pantoic acid and/or D-pantolactone include (6) a process which comprises optically resolving chemically synthesized DL-pantolactone with a resolving agent such as quinine and brucine, (7) a process which comprises decomposing only L-pantolactone in DL-pantolactone with a particular microorganism to obtain only D-pantolactone, (8) a process which comprises oxidizing only L-pantolactone in DL-pantolactone with a particular microorganism to obtain ketopantolactone, which is then asymmetrically reduced to D-pantolactone (JP-A 47-19745), (9) a process which comprises asymmetrically reducing chemically synthesized ketopantolactone with a particular microorganism to obtain D-pantolactone (JP-B 61-14797), (10) a process which comprises selectively and asymmetrically hydrolyzing L-pantolactone in DL-pantolactone with a particular microorganism to obtain D-pantolactone (JP-A 57-152895 and JP-A 62-294092), (11) a process which comprises selectively and asymmetrically hydrolyzing D-pantolactone in DL-pantolactone with a particular microorganism to obtain D-pantoic acid (JP-B 3-65198), and (12) a process which comprises culturing a particular microorganism to biosynthesize D-pantoic acid from glucose (JP-A 6-261772).

In industrial production of D-pantothenic acid (hereinafter including a salt thereof), above process (1) not only requires complicated steps to synthesize the main raw material DL-pantolactone, but also contains complicated and difficult optical resolution steps. Above process (2) disadvantageously needs a step for producing a D-pantothenic acid ester or DL-pantothenic acid ester from DL-pantolactone. Above process (3) disadvantageously uses expensive ATP and tris buffer, and it is an impractical process because it produces only a trace amount of pantothenic acid from the expensive starting material D-pantoic acid. Above process (4) is simpler than the other processes, but it requires steps for producing DL-pantoic acid and racemization. Above process (5) is more simplified than above process (4). However, the activity of the valine biosynthesis pathway located at the upstream of the pantothenic acid biosynthesis pathway disappears at the late stage of the culture, and the pantothenic acid production stops with depletion of valine. The production is thus limited.

Most of the processes for producing D-pantoic acid and/or D-pantolactone disadvantageously use the starting material DL-pantolactone that must be synthesized through complicated steps. In addition, above process (6) disadvantageously uses an expensive resolving agent and has difficulty in recovering D-pantolactone. Above process (7) is disadvantageous because half of the DL-pantolactone is lost. Above processes (8), (9), (10) and (11) have great difficulty in producing only D-isomer in 100% optical yield in the culture solution because of the characteristics of the microorganism to be used and the characteristics of pantolactone or pantoic acid. Furthermore, above processes (6), (10) and (11) requires additional complicated steps to recover and recycle the remaining L-isomer. The D-pantoic acid production in above process (12) depends on the activity of valine biosynthesis as in above pantothenic acid production process (5).

SUMMARY OF THE INVENTION

The present inventors have intensively studied to obtain an industrially advantageous and efficient process for producing D-pantothenic acid. As a result, in a process which comprises culturing a microorganism in a culture medium containing β-alanine to produce D-pantothenic acid, it has been found that a bacterial strain transformed with a plasmid containing a gene for branched amino acid biosynthesis can produce D-pantothenic acid or D-pantoic acid (and/or D-pantolactone) in the culture medium in higher concentrations. The introduction of the plasmid enhances the activity of valine biosynthesis at the early stage of the culture and maintains the enhanced activity during the middle and late stages. The pantothenic acid production thus continues longer, and the final accumulation of the product has been increased.

The present invention provides a process for producing D-pantoic acid or a salt thereof, which comprises culturing a microorganism transformed with a plasmid containing a DNA having a pantothenic acid biosynthesis gene region or a part thereof and a branched amino acid biosynthesis gene region or a part thereof to produce and accumulate D-pantoic acid or a salt thereof in the medium, and collecting the D-pantoic acid or a salt thereof.

The present invention also provides a process for producing D-pantothenic acid or a salt thereof, which comprises culturing a microorganism transformed with a plasmid containing a DNA having a pantothenic acid biosynthesis gene region or a part thereof and a branched amino acid biosynthesis gene region or a part thereof in the presence of β-alanine to produce and accumulate D-pantothenic acid or a salt thereof in the medium, and collecting the D-pantothenic acid or a salt thereof.

The present invention further provides a process for producing D-pantoic acid or a salt thereof, which comprises culturing a microorganism transformed with a plasmid containing a DNA having a pantothenic acid biosynthesis gene region or a part thereof and a plasmid containing a DNA having a branched amino acid biosynthesis gene region or a part thereof to produce and accumulate D-pantoic acid or a salt thereof in the medium, and collecting the D-pantoic acid or a salt thereof.

The present invention further provides a process for producing D-pantothenic acid or a salt thereof, which comprises culturing a microorganism transformed with a plasmid containing a DNA having a pantothenic acid biosynthesis gene region or a part thereof and a plasmid containing a DNA having a branched amino acid biosynthesis gene region or a part thereof in the presence of β-alanine to produce and accumulate D-pantothenic acid or a salt thereof in the medium, and collecting the D-pantothenic acid or a salt thereof.

In addition, the present invention provides a microorganism which is transformed with (a) a plasmid containing a DNA having a pantothenic acid biosynthesis gene region or a part thereof and a branched amino acid biosynthesis gene region or a part thereof, or (b) a plasmid containing a DNA having a pantothenic acid biosynthesis gene region or a part thereof and a plasmid containing a DNA having a branched amino acid biosynthesis gene region or a part thereof, and which can produce pantoic acid or produce pantothenic acid in the presence of β-alanine.

Preferably, the microorganism is *Escherichia coli* FV 5069/pFV202 (FERM BP-5227).

Furthermore, the present invention provides a plasmid which contains a DNA having a pantothenic acid biosynthesis gene region or a part thereof and a branched amino acid biosynthesis gene region or a part thereof.

Preferably, the plasmid is pFV202.

In the present invention, the branched amino acid biosynthesis gene region or a part thereof is preferably ilvGM gene.

The present invention can increase the valine production which is problematic in the above processes (5) and (12), thereby accumulating higher concentrations of pantothenic acid.

DETAILED DESCRIPTION OF THE INVENTION

Figure 1:
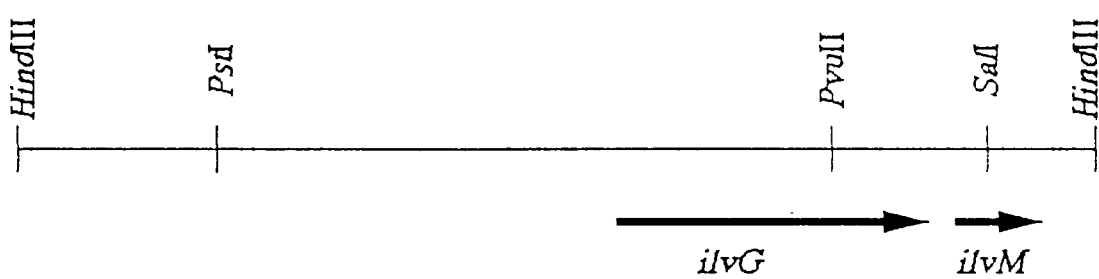
FIG. 1 is a restriction map of the 4.7 kb DNA fragment into which pFV 202 has been inserted.

In the present invention, D-pantoic acid, D-pantothenic acid and β-alanine may be in their salt forms. The terms "D-pantoic acid", "D-pantothenic acid" and "β-alanine" used herein include their salts as well as their free forms. Examples of the salts of D-pantothenic acid, D-pantothenic acid and β-alanine include salts with alkaline metals and alkaline earth metals. In each case, calcium salt, sodium salt or potassium salt is preferred.

The present inventors have studied to develop an efficient and economical process for producing D-pantoic acid from carbon sources such as saccharides by direct fermentation with a microorganism belonging to the genus Escherichia, etc. As a result, it has been found that a bacterial strain which is capable of producing a larger amount of D-pantoic acid is included in microorganisms treated by recombinant DNA technique to enhance not only their pantothenic acid biosynthesis pathway but also their valine biosynthesis pathway located at the upstream. It has been further found that a large amount of D-pantothenic acid can be produced by contacting such a microorganism with β-alanine in a culture medium containing carbon sources. That is, the process for producing D-pantoic acid or D-pantothenic acid of the present invention utilizes the capability of the microorganism to synthesize D-pantoic acid or D-pantothenic acid. Thereby, (a) D-pantoic acid is biosynthesized from various carbon sources such as glucose to accumulate it in the culture medium, or (b) β-alanine is contacted with the microorganism by, for example, adding β-alanine to the culture medium, to cause condensation of the biosynthesized D-pantoic acid with β-alanine to accumulate D-pantothenic acid in the medium. Thus, the process of the present invention can produce much higher concentrations of D-pantoic acid and D-pantothenic acid by enhancing the activity of not only the pantothenic acid biosynthesis pathway but also the valine biosynthesis pathway located at the upstream of it by the recombinant DNA technique.

The microorganisms to be used in the present invention include microorganisms which can produce D-pantothenic acid in the presence of β-alanine, and microorganisms which can produce D-pantoic acid. For practical use, the microorganisms are preferably microorganisms belonging to the family of Enterobacteriaceae, such as microorganisms belonging to the genera Citrobacter, Shigella, Klebsiella, Enterobacter, Salmonella and Escherichia. More preferred examples of the microorganisms include bacterial strains belonging the genus Escherichia, such as known strains of *Escherichia coli* listed in List of Cultures, 8th ed., 1988 (Institute for Fermentation, Osaka, Japan) (e.g., *Escherichia coli* IFO 3547) and strains derived therefrom. Examples of the derived strains include *Escherichia coli* strain FV 5069 obtained by providing *Escherichia coli* IFO 3547 with salicylic acid resistance, α-ketoisovaleric acid resistance, α-ketobutyric acid resistance, β-hydroxyaspartic acid resistance and o-methylthreonine resistance, *Escherichia coli* strain FV 5069/pFV 202 (FERM BP-5227) obtained by transforming *Escherichia coli* strain FV 5069 with plasmid pFV 202 containing a pantothenic acid biosynthesis gene region or a part thereof and a branched amino acid biosynthesis gene region or a part thereof.

The gene fragment containing the branched amino acid biosynthesis gene can be prepared by known methods described in, for example, H. Saito and K. Miura, Biochim. Biophys. Acta, or modified methods thereof. For example, the chromosomal DNA is extracted from the donor cells and then cleaved with the restriction enzyme HindIII. Then, the chromosomal DNA fragment thus obtained is inserted into the vector DNA. The vector DNA to be used in the present invention is appropriately selected from vector DNAs that can grow in the host cells. The vector DNAs that can grow in the host cells include, for example, pSC101 (Proc. Natl. Acad. Sci., U.S.A., 70, 3240 (1973)), and pUC18 (Gene, 33, 103 (1985)). These vector DNAs are not specifically limited, and those newly isolated or synthesized can be used so long as they can achieve the objective of the present invention. The gene fragment can be inserted into these plasmid vectors by known methods described in, for example, T. Maniatis et al., Molecular Cloning A Laboratory Manual, Cold Spring Harbor Laboratory, Todai Shuppankai (1982)), etc. or modified methods thereof. The plasmid into which the gene fragment have been inserted can be introduced into host cells by known transformation methods described in, for example, J. Mol. Biol., 53, 159 (1972), etc. or modified methods thereof. Examples of the host cells include known bacterial strains such as *Escherichia coli* strain JM109 (J. Mol. Biol., 166 (1983)).

The strain into which the plasmid containing the branched amino acid biosynthesis gene is introduced can be selected from the transformed strains by, for example, the colony hybridization technique, etc. using a part of acetohydroxy acid synthase gene sequence of *E. coli* strain K-12 as a probe. The plasmid DNA containing the branched amino acid biosynthesis gene thus obtained can be extracted from its host strain, and introduced into other host cells. Alternatively, the DNA fragment containing the branched amino acid biosynthesis gene can be prepared from the extracted plasmid DNA and then ligated to other vectors.

Examples of the transformed strains thus obtained include *Escherichia coli* strain FV 5069/pFV 202 (FERM BP-5227, IFO 15857). pFV 202 is a plasmid containing a pantothenic acid biosynthesis gene derived from *Escherichia coli* strain FV 525 and a branched amino acid biosynthesis gene derived from *Escherichia coli* strain FV 5069 (acetohydroxy acid synthase isozyme II gene). *Escherichia coli* strain FV 5069/pFV 202 (FERM BP-5227) is a strain obtained by introducing pFV 202 into *Escherichia coli* strain FV 5069. The IFO numbers used herein are accession numbers to Institute for Fermentation, Osaka (IFO) (17-5 Juso-honmachi 2-chome, Yodogawa-ku, Osaka-shi, Japan), and the FERM BP numbered used herein are accession numbers to National Institute of Bioscience and Human-Technology, Agency of Industrial Science and Technology (NIBH) (1-3, Higashi 1-chome, Tsukuba-shi, Ibaraki-ken, Japan) under the Budapest Treaty. In particular, *Escherichia coli* FV 5069/pFV 202 has been deposited at NIBH under the accession number FERM BP-5227 under the Budapest Treaty since Sep. 7, 1995.

The bacterial strains thus obtained can be cultured continuously or intermittently by conventional methods such as shaking culture (e.g., shaking culture on a rotary shaker), stationary culture and aeration and shaking culture. The culture medium to be used may have conventional formulation in which the microorganism to be used can grow. The carbon sources can appropriately be selected from assimilable carbon sources such as carbohydrates, oils and fats, fatty acids, organic acids and alcohols, and used alone or as mixtures of them. The nitrogen sources include, for example, organic nitrogen sources such as peptone, soybean flour, cotton flour, corn steep liquor, yeast extract, meat extract, malt extract and urea, and inorganic nitrogen sources such as ammonium sulfate, ammonium chloride, ammonium nitrate and ammonium phosphates. These nitrogen sources can be used alone or as mixtures thereof. It is advantageous that potassium dihydrogenphosphate or dipotassium hydrogenphosphate is used as a phosphorus source. The medium may contain metal salts necessary for the growth (e.g., magnesium sulfate), essential growth factors or growth-promoting substances such as amino acids and vitamins in addition to carbon sources, nitrogen sources and phosphorus sources. In order to control the pH during the culture, basic substances such as sodium hydroxide, potassium hydroxide, ammonia, calcium carbonate, etc., can appropriately be added. Addition of an anti-foaming agent is also effective to control foaming. These substances may appropriately be added during the culture. In order to maintain aerobic conditions, it is effective to conduct oxygen-enriched aeration. The temperature for the culture is normally 15° C. to 45° C., preferably 25° C. to 40° C. The culture is continued until the maximum accumulation of pantothenic acid and/or pantoic acid is obtained. Normally, a culture period of 6 hours to 120 hours can achieve this objective. In the production of D-pantothenic acid according to the present invention, the raw material β-alanine can be contacted with the bacterial cells by adding the raw material before the culture of the bacterial strains or at a suitable stage during the culture, or adding the raw material to processed bacterial cells. The processed bacterial cells mean rinsed bacterial cells of the culture obtained by culturing the bacteria, acetone-dried bacterial cells, bacterial cells immobilized with polyacrylamide gel or k-carrageenan, etc. The raw materials can be added in one portion or over a suitable period continuously or intermittently as a solution or suspension in a suitable solvent such as water or as powder.

The concentration of β-alanine to be added to the medium varies with the productivity of the microorganisms. From an economical point of view, the concentration of β-alanine is preferably 0.1 to 6 w/v%, more preferably 0.5 to 4 w/v%.

D-pantothenic acid or a salt thereof can be isolated from the above culture or reaction mixture by conventional methods. For example, after removing the bacterial cells from the culture, the reside is subjected to known isolation techniques such as ion-exchange chromatography, adsorption to activated charcoal, synthetic adsorbents, etc., concentration and crystallization to isolate D-pantothenic acid or a salt thereof. These techniques can be used alone or in combination. The crystallization according to JP-B 40-2330 is industrially advantageous because it can produce easily filterable crystals in high yield. According to this crystallization method, the solvated hydrate containing 4 mol of methanol and 1 mol of water per mol of calcium pantothenate (calcium pantothenate.4 MeOH.1H$_2$O) is obtained as precipitated crystals. Drying the resulting crystals removes the methanol and water in the crystals to give calcium pantothenate (M. Inagaki et al., Chem. Pharm. Bull., 24, 3097–3102 (1976)).

For example, calcium D-pantothenate can be isolated from the culture as follows. The culture from which the bacterial cells have been removed is passed through a column packed with a cation-exchange resin (e.g., Diaion PK-216 (H-form), PK-228 (H-form) manufactured by Mitsubishi Chemical Corporation) to remove cations, and then passed through a column packed with an anion-exchange resin (e.g., PA-412 (OH-form), WA-30 (OH-form) manufactured by Mitsubishi Chemical Corporation) to remove inorganic anions and organic acids having stronger acidities than pantothenic acid. Calcium hydroxide is added to the eluate (pH:about 2.6) containing free pantothenic acid to adjust the pH to about 5.0, and then the mixture is concentrated to a pantothenic acid concentration of about 25 w/v%. Then, calcium hydroxide is added to the concentrate to adjust the pH to about 7.0, and activated charcoal (e.g., Shirasagi A manufactured by Takeda Chemical Industries, Ltd.) is added for decolorization. After the activated charcoal is removed by filtration, the filtrate is concentrated to a calcium pantothenate concentration of about 45% to 55% (w/w). Then, an appropriate amount of methanol is added to adjust the water content in the solution to 5% to 15%. Then, the solution is cooled to about 2° C., and seed crystals are added to precipitate crystals of solvated hydrate of calcium pantothenate. The crystals are collected and dried to obtain high purity of D-pantothenic acid in high yield.

EXAMPLES

The following examples further illustrate the present invention in detail but are not to be construed to limit the scope thereof.

D-pantothenic acid was determined by high performance liquid chromatography (column: Shimadzu SCR101H (7.9 mm I.D.×30 cm); mobile phase: 0.008N sulfuric acid; flow rate: 0.8 ml/min; detection: differential refractometer) and/or bioassay (test bacteria: *Lactobacillus plantarum* IFO 3070; medium: commercially available medium for quantifying pantothenic acid (manufactured by DIFCO)). Valine in the culture was determined by high performance liquid chromatography (column: Mitsubishi Chemical Corporation MCI GEL CRS 10 W (4.6 mm I.D.×5 cm); mobile phase: 1mM-CuSO$_4$/CH$_3$CN=7/1; flow rate: 0.7 ml/min; detection: UV photometer).

EXAMPLE 1

(1) Preparation of chromosomal DNA

*Escherichia coli* FV5069 was inoculated in L medium (1 liter) (bactotryptone 10%, yeast extract 0.5%, sodium chloride 0.5%) and incubated at 37° C. overnight. From the resulting bacterial cells, the chromosomal DNA (final yield: 3.3 mg) was obtained by the method of Saito et al. (Biochim. Biophys. Acta., 72, 619 (1963)) using phenol.

(2) Insertion of the chromosomal DNA into the vector plasmid pUC18

Each of the chromosomal DNA (10 µg) obtained in above (1) and pUC18 (manufactured by Nippon Gene) was cleaved with the restriction enzyme HindIII (manufactured by Nippon Gene), and the resulting DNA fragments were mixed and ligated with a DNA ligase derived from T4 phase (Nippon Gene).

(3) Selection of a plasmid DNA into which the chromosomal DNA fragment has been inserted

*Escherichia coli* strain JM109 was transformed with a mixture of the various plasmids obtained in above (2) by the competent cell method. Then, a suspension containing this transformant was spread on an L agar plate medium containing ampicillin sodium salt (50 µg/ml), IPTG (0.5 mM) and X-gal (100 µg/ml) and incubated at 37° C. overnight. Among the resulting colonies, the white colonies were selected as transformants with the plasmid DNA containing the chromosomal DNA fragment.

(4) Preparation of probes

About 600 bp sequence of *E. coli* strain K-12 ilvG gene determined by Rother et al. (acetohydroxy acid synthase isozyme II large subunit gene, Nucleic Acids Research, 2137, 15 (1987)) was amplified by the PCR method. The amplified genes were labelled with $^{32}$P by the random prime method, and used as probes.

(5) Cloning of acetohydroxy acid synthase isozyme II gene

A nylon membrane was placed on an L agar plate medium containing ampicillin sodium (50 µg/ml), streaked with the white colony obtained in above (3), and incubated at 37° C. overnight. The membrane was treated with an alkali, neutralized, and baked at 80° C. for 2 hours to fix the intracellular DNA on the membrane. By using the probe of above (4), the membrane was subjected to hybridization to obtain one strain of a colony emitting an apparently stronger signal than the others.

(6) Confirmation by Southern hybridization

A plasmid (10 µg) was extracted from the above colony, cleaved with HindIII and subjected to electrophoresis. The inserted fragment was analyzed by Southern hybridization. The results showed that this fragment was 4.7 kb long (the HindIII fragment containing acetohydroxy acid synthase isozyme II gene of K-12 is also 4.7 kb long) and strongly hybridized with the probe obtained in above (4).

(7) Construction of an expression plasmid

After the above 4.7 kb inserted fragment was inserted into the HindIII site of the plasmid vector pMW 118, 2.5 kb of the pantothenic acid biosynthesis gene of *Escherichia coli* FV525 was inserted into the EcoRI site. The resulting plasmid was designated as pFV202. The pantothenic acid-producing strain FV5069 was transformed with this plasmid, and the resulting transformant was designated as FV5069/pFV202. The acetohydroxy acid synthase isozyme II activity of this transformant was compared with that of FV5069/pFV31 transformed with pFV31 into which only pantothenic acid biosynthesis gene was inserted, and that of the parent (host) strain FV5069 which was not transformed.

(8) Determination of the acetohydroxy acid synthase activity of the transformant The test bacteria were incubated in the production medium (A) for about 48 hours, and a lysate was prepared from the bacteria by sonication. The lysate was centrifuged at 20,000 rpm for 1 hour to obtain a supernatant. According to the method of Jackson et al. (Methods Enzymol. 1988), the resulting acetolactic acid was converted to acetoin using the supernatant as a crude enzyme solution. The resulting acetoin was colored with 2-naphthol and quantified at a wavelength of 530 nm.

The results are shown in Table 1.

As seen from Table 1, the 4.7 kb HindIII fragment inserted into pFV202 contains ilvGM gene which encodes acetohydroxy acid synthase isozyme II.

TABLE 1

| Bacterial strain | Specific activity (µmol/min. mil) |
|---|---|
| FV5069 | 38.2 |
| FV5069/pFV31 | 35.7 |
| FV5069/pFV202 | 108.9 |

(9) Restriction map of the 4.7 kb fragment containing ilvGM

The 4.7 kb DNA fragment inserted into pFV202 contains one PstI site, one SalI site and one PvuII site. FIG. 1 shows a restriction map of the fragment.

EXAMPLE 2

The liquid medium having the composition shown in Table 2 was sterilized by heating at 121° C. for 15 minutes in an autoclave, and dispensed in 20 ml portions into 200 ml Erlenmeyer flasks. In the medium, one platinum loop of each of *Escherichia coli* strain FV5069/pFV202 (FERM BP-5227) and strain FV5069/pFV31 (FERM BP-4395) obtained from a slant medium of above (7) of Example 1 was inoculated, and incubated at 30° C. for 20 hours on a rotary shaker at 220 rpm. The seed culture (1 ml) was transferred to a medium (20 ml) with having the composition shown in Table 2, and incubated with shaking at 38° C. for 72 hours in a 200 ml creased Erlenmeyer flask. During the incubation, various substances were added as shown in Table 3. Table 4 shows the amount of the produced pantothenic acid (PaA) and the amount of valine (Val) at the end of the culture.

TABLE 2

| Medium composition: | |
|---|---|
| Seed medium: | |
| CSL | 0.5% |
| (NH$_4$)$_2$SO$_4$ | 0.5% |
| MgSO$_4$.7H$_2$O | 0.001% |

TABLE 2-continued

Medium composition:

| | |
|---|---|
| $KH_2PO_4$ | 0.01% |
| $K_2HPO_4$ | 0.01% |
| Thiamin hydrochloride | 2 µg/ml |
| Glucose | 5% |
| $CaCO_3$ | 2% |
| pH | 7.0 |

Main medium:

| | |
|---|---|
| CSL | 2% |
| $(NH_4)_2SO_4$ | 1.25% |
| $MgSO_4 \cdot 7H_2O$ | 0.002% |
| $KH_2PO_4$ | 0.01% |
| β-alanine | 1% |
| Thiamin hydrochloride | 0.5 µg/ml |
| Glucose | 9% |
| $CaCO_3$ | 4% |
| pH | 7.0 |

TABLE 3

Addition of various substances

| Culture time | Glucose | Thiamin hydrochloride | $(NH_4)_2SO_4$ | β-alanine |
|---|---|---|---|---|
| 17 hours | 6% | 0.5 µg/ml | | 1% |
| 24 hours | 6% | 0.5 µg/ml | 0.75% | 0.5% |
| 41 hours | 4% | 0.5 µg/ml | | 0.5% |
| 50 hours | 5% | 0.5 µg/ml | | |

TABLE 4

Results of the culture

| | FV5069/pFV31 | | FV5069/pFV202 | |
|---|---|---|---|---|
| Culture time | PaA | Val | PaA | Val |
| 24 hours | 38.7 g/L | 2.1 g/L | 29.9 g/L | 5.2 g/L |
| 48 hours | 52.5 g/L | 1.1 g/L | 60.1 g/L | 2.7 g/L |
| 72 hours | 51.8 g/L | 0.9 g/L | 66.0 g/L | 1/3 g/L |

*Escherichia coli* FV5069/pFV31 has been deposited at the above-described NIBH (National Institute of Bioscience and Human-Technology, Agency of Industrial Science and Technology; 1-3, Higashi 1-chome, Tsukuba-shi, Ibaraki-ken, Japan) under the accession number of FERM BP-4395 under the Budapest Treaty since Aug. 30, 1993.

As described above, the process of the present invention can enhance the activity of the valine biosynthesis pathway located at the upstream of the biosynthesis pathways of pantoic acid and pantothenic acid to increase valine productivity, and can produce higher concentrations of pantoic acid and pantothenic acid. Thus, the process of the present invention is an industrially advantageous and efficient process.

We claim:

1. A process for producing D-pantothenic acid or a salt thereof comprising:

culturing *Escherichia coli* FV 5069/pFV202 (FERM BP-5227) in the presence of β-alanine to produce D-pantothenic acid or a salt thereof; and isolating D-pantothenic acid or a salt thereof.

2. A purified culture of *Escherichia coli* FV 5069/pFV202 (FERM BP-5227).

3. A plasmid which is pFV202.

* * * * *